United States Patent
Okamoto

(10) Patent No.: US 7,189,412 B2
(45) Date of Patent: Mar. 13, 2007

(54) FENOFIBRATE-CONTAINING COMPOSITION

(75) Inventor: Masaru Okamoto, Hamura (JP)

(73) Assignee: ASKA Pharmaceutical Co., Ltd., Tokyo (JP)

( * ) Notice: Subject to any disclaimer, the term of this patent is extended or adjusted under 35 U.S.C. 154(b) by 332 days.

(21) Appl. No.: 10/469,305

(22) PCT Filed: Feb. 28, 2002

(86) PCT No.: PCT/JP02/01850

§ 371 (c)(1), (2), (4) Date: Aug. 29, 2003

(87) PCT Pub. No.: WO02/069957

PCT Pub. Date: Sep. 12, 2002

(65) Prior Publication Data

US 2004/0071771 A1    Apr. 15, 2004

(30) Foreign Application Priority Data

Mar. 1, 2001  (JP) ............................. 2001-056104

(51) Int. Cl.
*A61K 9/64* (2006.01)

(52) U.S. Cl. ................... 424/456; 424/456; 514/962

(58) Field of Classification Search ............... 424/456, 424/70.22

See application file for complete search history.

(56) References Cited

U.S. PATENT DOCUMENTS

| 4,895,726 A | * | 1/1990 | Curtet et al. ............. 424/456 |
| 5,827,536 A | | 10/1998 | Laruelle .................. 424/451 |
| 6,074,670 A | * | 6/2000 | Stamm et al. ............. 424/462 |

FOREIGN PATENT DOCUMENTS

| EP | 0 904 781 | 3/1999 |
| JP | 5-194209 | 8/1993 |

* cited by examiner

*Primary Examiner*—Michael G. Hartley
*Assistant Examiner*—Nabila Ebrahim
(74) *Attorney, Agent, or Firm*—Wenderoth, Lind & Ponack, L.L.P.

(57) ABSTRACT

A novel fenofibrate-containing composition having equivalent bioavailability, when compared to conventional capsules, is effective in reducing the size of the conventional capsule preparations. The fenofibrate-containing composition comprises the following formula:

| (a) fenofibrate | 100 parts by weight, |
| (b) a solid surfactant | 3 to 4 parts by weight, |
| (c) lactose | 1 to 2 parts by weight, and |
| (d) magnesium stearate | 1 to 2 parts by weight, | in admixture with a binder and a disintegrator, wherein the sum of said binder and said disintegrator is 17 to 20 parts by weight, and the fenofibrate and the solid surfactant are co-micronizates.

4 Claims, 1 Drawing Sheet

FENOFIBRATE-CONTAINING COMPOSITION

This application is a U.S. national stage of International Application No. PCT/JP02/01850 filed Feb. 28, 2002.

TECHNICAL FIELD

The present invention relates to a pharmaceutical composition which is effective in reducing the size of fenofibrate-containing preparations (i.e., in minimizing fenofibrate-containing dosage forms).

BACKGROUND ART

Fenofibrate, a compound with the chemical name of isopropyl 2-[4-(4-chlorobenzoyl)phenoxy]-2-methylpropionate, lowers the levels of serum cholesterol, LDL-cholesterol, and triglyceride, and raises HDL-cholesterol levels. Fenofibrate has been appreciated, worldwide including in Japan, as an antihyperlipidemic agent which improves overall lipid metabolism.

Fenofibrate has been conventionally formulated as a hard capsule form (hereinafter, may be briefly referred to as "capsule"). Fenofibrate compositions with improved bioavailability have been studied. For example, Japanese Examined Patent Publication No. Hei 7-14876 (JP 7-14876, B (1995)) has disclosed the composition containing a homogeneous mixture of co-micronized particles (hereinafter, may be referred to as "co-micronizate") of fenofibrate and a solid surfactant.

Generally, when a drug must be orally taken over a long period of time, first, the fewer number of capsule per dose as well as preparations of easily ingestable size greatly leads to improvement of patient's compliance with drug-taking. Such improvement of the drug-taking compliance becomes more important especially in the case of the elderly who experience hypofunction in swallowing.

For hyperlipemia, an indication to which the fenofibrate preparations are applied, in most cases, patients are required to take the drug over a long period of time such as a yearly basis, also a majority of the patients are elderly persons, and further there are lots of cases where several types of concomitant drugs are frequently prescribed due to complications with diabetes and arteriosclerosis. Under such circumstances, it has been strongly desired to develop minimized and easily ingestable preparations without increasing the number of capsule per dose.

In the case of the above prior art composition containing the co-micronizate of fenofibrate and the solid surfactant (hereinafter, referred to as "co-micronized composition"), it enables the improvement in bioavailability, leading to the reduction of 300 mg fenofibrate dosage per day to ⅔, 200 mg. However, even in the case of such co-micronized compositions, when formulated, pharmaceutical additives such as an excipient, a binder and a disintegrator (hereinafter, also simply referred to as additives) are required to be added. In the above prior art, the total amount of fenofibrate and the additives per capsule for the capsule preparation containing 200 mg of co-micronizate of fenofibrate becomes approximately 297 to 350 mg (the preparation examples I and II in Japanese Examined Patent Publication No. Hei 7-14876 (JP 7-14876, B (1995))). To fill up them in one capsule, there is no other choice than to use the size No. 1 capsule (major axis: approx. 19.1 mm and minor axis: 6.9 mm) or larger one.

Currently, capsules available for pharmaceutical use are supplied in 8 sizes, i.e., the hard capsules are numbered from the size No. 000 (the largest size with major axis: approx. 26.0 mm and minor axis: 10.0 mm) to the size No. 5 (the smallest size with major axis: 11.1 mm and minor axis: 4.9 mm) (see: for example, Otsuka, A. et al. (Ed.), "SEIZAIGAKU (4th Edition)", p. 91, Nankodo Co. Ltd., Japan, 1990; Murata, T. et al. (Ed.), "YAKUZAIGAKU (revised 5th Edition)", p. 130, Nankodo Co. Ltd., Japan, 1997). However, when the patients take the drug orally, the smaller the capsule size and the fewer number of the capsule per dose, the less the patient's burden, which leads improvement in patient's compliance. Thus, in many cases, the capsules equal to or smaller than size No. 2 (major axis: approx. 17.6 mm and minor axis: 6.4 mm) have been favorably used. However, although it became possible to make the co-micronized composition to reduce the amount of the active ingredient to ⅔, neither pharmaceutical formulation nor technology has been found that allows 200 mg of fenofibrate which is a dose per day to be filled into one capsule equal to or smaller than the size No. 2 capsule.

DISCLOSURE OF THE INVENTION

Thus, the present inventor has extensively carried out a research into various pharmaceutical additives and their amounts to be admixed when the fenofibrate-containing composition, especially the fenofibrate composition suitable for capsule preparations, is prepared, and studied minimization of the capsule preparations without changing the bioavailability of fenofibrate which is the active ingredient. As a result, the present inventor has succeeded in finding a novel composition which enables the reduction of a total additive amount to ½ or less relative to the conventional capsule preparation containing the co-micronized composition (hereinafter, "conventional capsule"), by incorporating specific additives, and by specific compounding ratio with a co-micronized composition, and the production of minimized capsule preparations (for example, down-sizing to shift conventional size No. 1 capsules into size No. 2 or size No. 3, similarly size No. 2 capsules into size No. 3, and size No. 3 capsules into size No. 4). Said novel composition is expected to have equivalent bioavailability in vivo when compared to the conventional capsules. A preferable condition for achieving the object of the present invention is described herein below.

The present invention provides a fenofibrate-containing composition comprising the following formula:

| | |
|---|---|
| (a) fenofibrate | 100 parts by weight, |
| (b) a solid surfactant | 3 to 4 parts by weight, |
| (c) lactose | 1 to 2 parts by weight, and |
| (d) magnesium stearate | 1 to 2 parts by weight, | in admixture with a binder and a disintegrator, wherein the sum of said binder and said disintegrator is 17 to 20 parts by weight, and the fenofibrate and the solid surfactant are co-micronizates.

BEST MODES FOR CARRYING OUT THE INVENTION

Figure 1:
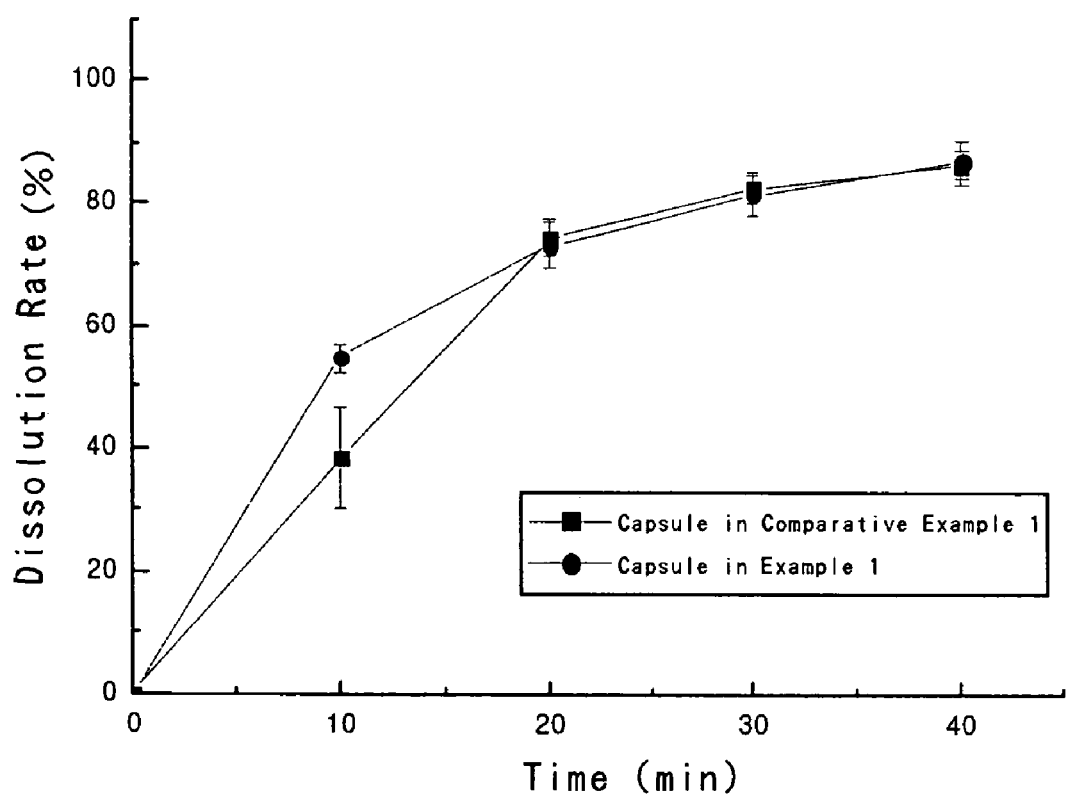
FIG. 1 shows the results of Test Example 1.

The fenofibrate used in the present invention has been previously co-micronized with the solid surfactant. The above solid surfactant used includes alkali metal sulfates of lauryl alcohol (e.g., sodium lauryl sulfate), copolymers of ethylene oxide/propylene oxide (e.g., polyoxyethylene (105) polyoxypropylene (5) glycol), sucrose fatty acid esters and the like. Among them, sodium lauryl sulfate is advantageously used.

The amount of the above solid surfactant is 3 to 4 parts by weight based on 100 parts by weight of fenofibrate. Both fenofibrate and the solid surfactant are co-micronized by a micronizer typically used in manufacturing preparations (e.g., a jet mill, a hammer mill, a vibrating ball mill). Co-micronization can be carried out according to, for example, the method described in Japanese Examined Patent Publication No. Hei 7-14876 (JP 7-14876, B (1995)). It is advantageous that the co-micronization is performed until obtaining powder where the mean particle size of the micronized powder is less than 15 μm, preferably less than 10 μm, and especially preferably less than 5 μm.

The above lactose could be any of those which are at the grade typically used as pharmaceutical additives. The amount of the lactose used is from 1 to 2 parts by weight based on 100 parts by weight of fenofibrate. The above magnesium stearate could be any of those which are at the grade typically used as pharmaceutical additives. The amount of the magnesium stearate used is from 1 to 2 parts by weight based on 100 parts by weight of fenofibrate.

As the above binder, starch is advantageously used. The starch used for the invention may be any of those which are at the grade typically used as pharmaceutical additives. The preferred starch includes α-modified starch, partially α-modified starch, wheat starch, corn starch, potato starch and soluble starch. The especially preferable starch is α-modified starch.

The above disintegrator preferably used includes crospovidone (otherwise known as: crosslinked poly vinylpyrrolidone), carmellose, sodium carmellose, potassium carmellose and the like which are at the grade typically used as pharmaceutical additives. The especially preferable disintegrator is crospovidone. The total amount of the above binder and disintegrator is 17 to 20 parts by weight based on 100 parts by weight of fenofibrate.

The composition of the present invention is prepared by the following process with adding the above additives to the above co-micronizate of fenofibrate and the solid surfactant:

The co-micronizate is mixed homogeneously with the additives, and subjected to a granulation process to form granules. A lubricant is further added thereto, followed by admixing, and the resultant is filled up in a vacant capsule to give the capsulated preparation. The granulation method may be a dry-granulation method or a wet-granulation method.

The composition obtained by the present invention, after formulated into a capsulated preparation, was subjected to a test according to the Dissolution Test as set forth in "The Japanese Pharmacopoeia, 13 Edition" (JP XIII) as described herein below. Consequently, for the composition obtained in the invention, even though an amount of the additives used was reduced to approximately ½ or less, no difference in a dissolution rate was found as compared with the conventional capsule preparations disclosed in Japanese Examined Patent Publication No. Hei 7-14876 (JP 7-14876, B (1995)), suggesting that it exhibits good bioavailability.

EXAMPLES

Described below are examples, including a comparative example and a test example, of the present invention which are provided only for illustrative purposes, and not to limit the scope of the present invention. All of the examples, the comparative example and the test example were carried out or can be carried out, unless otherwise disclosed herein specifically, by standard techniques which are well known and conventional to those skilled in the art.

Example 1

According to the preparation example I in Japanese Examined Patent Publication No. Hei 7-14876 (hereinafter referred to "PREPARATION I"), granules were prepared via a co-micronizing process of fenofibrate and sodium lauryl sulfate, wherein the formulation used was as follows:

Formula (in a capsule; total amount: 250.0 mg)

| | |
|---|---|
| Fenofibrate | 200.0 mg |
| Sodium lauryl sulfate | 7.0 mg |
| Lactose | 3.0 mg |
| Magnesium stearate | 3.0 mg |
| α-Modified starch | 30.0 mg |
| Crospovidone | 7.0 mg |

The granules thus obtained were filled into size No. 2 capsules.

Example 2

In the same manner as in Example 1, granules were prepared via a co-micronizing process of fenofibrate and sodium lauryl sulfate, wherein the formulation used was as follows:

Formula (in a capsule; total amount: 250.0 mg)

| | |
|---|---|
| Fenofibrate | 200.0 mg |
| Sodium lauryl sulfate | 7.0 mg |
| Lactose | 3.0 mg |
| Magnesium stearate | 3.0 mg |
| α-Modified starch | 30.0 mg |
| Low substituted hydroxypropyl cellulose | 7.0 mg |

The granules thus obtained were filled into size No. 2 capsules.

Example 3

In the same manner as in Example 1, granules were prepared via a co-micronizing process of fenofibrate and sodium lauryl sulfate, wherein the formulation used was as follows:

Formula (in a capsule; total amount: 250.0 mg)

| | |
|---|---|
| Fenofibrate | 200.0 mg |
| Sodium lauryl sulfate | 7.0 mg |
| Lactose | 5.0 mg |
| Magnesium stearate | 3.0 mg |
| α-Modified starch | 25.0 mg |
| Crospovidone | 10.0 mg |

The granules thus obtained were filled into size No. 2 capsules.

Comparative Example 1

In the same manner as in Example 1, granules were prepared via a co-micronizing process of fenofibrate and sodium lauryl sulfate, wherein the formulation used was as follows:

Formula (in a capsule; total amount: 350.0 mg)

| | |
|---|---|
| Fenofibrate | 200.0 mg |
| Sodium lauryl sulfate | 7.0 mg |
| Lactose | 101.0 mg |
| Magnesium stearate | 5.0 mg |
| α-Modified starch | 30.0 mg |
| Crospovidone | 7.0 mg |

The granules thus obtained were filled into size No. 1 capsules.

Test Example 1

Dissolution Test

<Test Method>

According to the Dissolution Test, Method 2 (Puddle method) under the "General Tests, Processes and Apparatus" as set forth in "JP XIII", the dissolution test for the capsules obtained in Example 1 and Comparative Example 1 was carried out using 1000 mL of 0.1 mol/L sodium lauryl sulfate as a dissolution medium at 50 rpm/min.

<Results>

The results are shown in FIG. 1. As is obviously shown in FIG. 1, no significant difference in the dissolution profile of fenofibrate was observed between Example 1 and Comparative Example 1.

INDUSTRIAL APPLICABILITY

As aforementioned, the fenofibrate-containing composition of the present invention retaining enhanced bioavailability when compared to conventional capsule preparations, allows reduction of additive amounts to ½ or less, and makes it possible to provide minimized capsules which can be easily taken by patients orally. Stating more specifically, the co-micronized fenofibrate composition containing 200 mg of fenofibrate conventionally requires larger capsules (e.g., size No. 1 capsules); however, the present invention enables the co-micronized fenofibrate composition to be filled into smaller capsules (e.g., size No. 2 or No. 3 capsules).

While the present invention has been described specifically in detail with reference to certain embodiments and examples thereof, it would be apparent that it is possible to practice it in other forms. In light of the disclosure, it will be understood that various modifications and variations are within the spirit and scope of the appended claims.

What is claimed is:

1. A fenofibrate-containing composition comprising the following formulation:

| | |
|---|---|
| (a) fenofibrate | 100 parts by weight, |
| (b) a solid surfactant | 3 to 4 parts by weight based on 100 parts by weight of fenofibrate, |
| (c) lactose | 1 to 2 parts by weight based on 100 parts by weight of fenofibrate, |
| (d) magnesium stearate | 1 to 2 parts by weight based on 100 parts by weight of fenofibrate, | in admixture with a binder and a disintegrator,
wherein the sum of said binder and said disintegrator is 17 to 20 parts by weight based on 100 parts by weight of fenofibrate, and the fenofibrate and the solid surfactant are co-micronizates,
wherein the composition is in the form of a capsule, and wherein the capsule is size No. 2 to size No. 4.

2. The composition according to claim 1, wherein the solid surfactant is sodium lauryl sulfate.

3. The composition according to claim 2, wherein the binder is starch.

4. The composition according to claim 3, wherein the disintegrator is crospovidone.

\* \* \* \* \*